(12) United States Patent
Langer et al.

(10) Patent No.: US 6,800,296 B1
(45) Date of Patent: Oct. 5, 2004

(54) MODIFICATION OF SURFACES USING BIOLOGICAL RECOGNITION EVENTS

(75) Inventors: Robert S. Langer, Newton, MA (US); Scott M. Cannizzaro, Cotuit, MA (US); Bernhard G. Mueller, Basel (CH); Kevin Shakesheff, Derby (GB)

(73) Assignee: Massachusetts Institute of Technology, Cambridge, MA (US)

(*) Notice: Subject to any disclaimer, the term of this patent is extended or adjusted under 35 U.S.C. 154(b) by 0 days.

(21) Appl. No.: 09/314,540

(22) Filed: May 19, 1999

(51) Int. Cl.[7] ........................... A61K 9/14; A61K 47/48
(52) U.S. Cl. ................. 424/484; 424/179.1; 424/194.1; 424/423; 424/486; 424/488; 424/489; 424/501; 514/2
(58) Field of Search ................. 424/502, 812, 424/1.33, 178.1, 179.1, 180.1, 181.1, 194.1, 78.07, 423, 424, 425, 426, 450, 484, 485, 486, 487, 488, 489, 500, 501; 514/2, 8, 12, 21; 435/7.1, 7.5; 536/23.1; 530/391.5, 391.9, 403, 404, 405, 406, 408, 409, 410, 411; 436/518, 523, 528, 529, 530, 531, 532, 533, 534, 535

(56) References Cited

U.S. PATENT DOCUMENTS

| | | | | |
|---|---|---|---|---|
| 4,427,781 A | * | 1/1984 | Masson et al. | 436/509 |
| 4,948,590 A | | 8/1990 | Hawrot et al. | 424/450 |
| 5,273,900 A | * | 12/1993 | Boyce | 435/240.23 |
| 5,374,516 A | | 12/1994 | Sutton et al. | 435/5 |
| 5,512,294 A | * | 4/1996 | Li et al. | 424/450 |
| 5,869,232 A | * | 2/1999 | Sallberg | 435/5 |
| 6,007,845 A | * | 12/1999 | Domb et al. | 424/501 |
| 6,254,890 B1 | * | 7/2001 | Hirosue et al. | 424/490 |

FOREIGN PATENT DOCUMENTS

| | | |
|---|---|---|
| DE | 19618926 | 11/1997 |
| EP | 0 700 933 | 3/1996 |
| WO | WO 9222332 | 12/1992 |
| WO | WO 97/46267 | 12/1997 |
| WO | WO 99/36107 | 7/1999 |

OTHER PUBLICATIONS

Bhat et al. J. Biomedical Materials Research. 40(1): 57–65, Apr. 1998.*
Patel et al. FASEB J. 12: 1447–1454, Nov. 1998.*
Branch, A.D. TIBS 23: 45–50, Apr. 1998.*
Hubbell, J.A., Biotechnology,(1995), 13:565.
Hynes, et al., Cell,(1992), 69:11.
Wright, et al., Biotechnology,(1995), 13:165.
Langer, et al., Science,(1993), 260:920.
Lynch, et al., Biotechnology and Bioengineering,(1996), 50:169.
Marshall, et al., British Journal of Cancer,(1996), 73:565.
Pande, et al., Bioconjugate Chemsitry, (1996), 7:159.
Ground, et al., Nature, (1996), 384:364.

(List continued on next page.)

*Primary Examiner*—Jeffrey Edwin Russel
(74) *Attorney, Agent, or Firm*—Choate, Hall & Stewart (57) ABSTRACT

The present invention provides a novel surface engineering strategy that uses biomolecular interactions to immobilize surface modifying ligands on biomaterial architectures. The surface modified compositions resulting from the inventive method are useful in many contexts, including, but not limited to, scaffolds for tissue engineering and as vehicles for site specific drug delivery. In one preferred embodiment, the biomolecular interaction is achieved by using an "anchor-adapter-tag" system, in which an adapter which can interact specifically and with high selectivity with an anchor molecule (present on the biodegradable surface) and a tag (bound to the ligand to be immobilized) simultaneously is used in attaching the ligand to the surface in a manner which is stable in vitro or in vivo. In another preferred embodiment, the biomolecular interaction is achieved by using an "anchor-tag" system, in which the anchor simultaneously acts to effect attachment to the architecture and mediate direct interaction with the tag.

11 Claims, 4 Drawing Sheets

OTHER PUBLICATIONS

Peppas, et al., Science(1994), 263:1715.
Pierschbacher, et al., Proc. Natl. Acad. Sci., U.S.A., (1984), 81:5885.
Ratner, B.D., Journal of Molecular Recognition,(1996), 9:617.
Shakesheff, et al., J. Colloid Interface Sci,(1997), 185:538.
Sultzbaugh, K. J., Journal of Microencapsulation,(1996) 13:363.
Wong, et al., Science, (1997), 275:820.
Yamada, et al., J. Biol. Chem. (1991), 266:12809.
Barrera, et al., J. Am. Chem. Soc., (1993), 115:11010.
Beer, et al., Blood (192), 78:117.
Cannizzaro, et al., Biotechnology and Bioengineering, (1998), 58:529.
Patel, et al., The FASEB Journal(1998),12:1447.
Chen, et al., Macromolecules,(1998), 31:2278.
Davies, et al., Langmuir, (1994), 10:2654.
Desai, et al., Macromolecules,(1992), 25:226.
Diamaudis, et al., Clinical Chemistry,(1991), 37:625.
Gonzalez, et al., J. Biol. Chem.,(1997),272:11288.
Han, et al., Macromolecules,(1996),29:5233.
Hoffman, Artificial Organs,(1992), 16:43.

* cited by examiner

PLA-PEG-Biotin

PLA-PEG-Biotin incubated with
avidin & biotin-G(11) GRGDS

FIG. 5

```
                        SEQUENCE LISTING

<160> NUMBER OF SEQ ID NOS: 3

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence:Found in B1
      chain of laminin, binds 67 kDa laminin receptor.

<400> SEQUENCE: 1

Tyr Ile Gly Ser Arg
 1               5

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence:Found in a
      chain of laminin, binds 110 kDa laminin receptor.

<400> SEQUENCE: 2

Ile Lys Val Ala Val
 1               5

<210> SEQ ID NO 3
<211> LENGTH: 16
<212> TYPE: PRT
<213> ORGANISM: Artificial Sequence
<220> FEATURE:
<223> OTHER INFORMATION: Description of Artificial Sequence:Peptide
      containing cell binding RGD sequence produced
      using standard laboratory techniques.

<400> SEQUENCE: 3

Gly Gly Gly Gly Gly Gly Gly Gly Gly Gly Gly Gly Arg Gly Asp Ser
 1               5                  10                  15
```

MODIFICATION OF SURFACES USING BIOLOGICAL RECOGNITION EVENTS

GOVERNMENT SUPPORT

The present research was supported by a grant from the National Institutes of Health (Grant Number 3F32GM17658-02S1).

BACKGROUND OF THE INVENTION

Biomaterials, defined as substances other than food or drugs contained in therapeutic or diagnostic systems that are in contact with tissue or biological fluids, play a crucial role as implants, diagnostics, devices for controlled delivery, and extracorporeal devices to name a few (see, Peppas, N. A.; Langer, R., Science, 1994, 263, 1715). One of the most significant problems for the use of devices fabricated from traditional biomaterials is the difficulty in engineering these surfaces to mediate interactions between cells and the biomaterials. The ability to design specific biomaterials, however, necessitates information about the molecular nature of surfaces of cells. Fortunately, advances in our knowledge of biochemical interactions at cell surfaces have led to structure elucidation of ligand molecules that bind to cell surface receptors and influence cell behavior (see, Yamada, K. M. J. Biol. Chem. 1991, 266, 12809; Koivunen et al., Biotechnology, 1995, 13, 165; Pasqualini et al., Nature, 1996, 364). Obtaining this information about the molecular nature of the surface of cells has enabled the development of novel materials for in vitro and in vivo biotechnology applications including the ligands that bind to cell surface receptors. (Hoffman, A. S., Artificial Organs, 1992, 16,43; Peppas, N. A. and Langer, R. S., Science, 1994, 263, 1715; Han, D. K. and Hubbell, J. A., Macromolecules, 1996, 29, 5233; Schaffer et al., Tissue Eng., 1997, 3, 53). Currently, the vast majority of ligand coupling to materials is through covalent attachment of ligands to the bulk polymer. However, attachment to the bulk is often inefficient when the end goal is surface derivatization. For example, many existing biodegradable polymers lack reactive groups that can be used to couple biological molecules to fabricated surfaces (Desai, N. P. and Hubbell, J. A., Biomaterials, 1991, 12, 144; Barrera et al., J. Am. Chem. Soc., 1993, 115, 11010). Even if such reactive groups are available, covalent strategies cannot be applied in all circumstances due to harsh reaction conditions and inefficient coupling or purification methods. In addition, reactive surface functionalities may be masked by surfactants used during system fabrication. Finally, very few techniques are universally applicable to any class of ligand (e.g., peptide, oligosaccharide, lipid) and do not damage the material or the ligand.

Clearly, there remains a need to improve the interactions between cells and biomaterial architectures. It would be most desirable to develop a system in which virtually any class of ligand could be efficiently coupled to a wide range of biomaterial architectures.

SUMMARY OF THE INVENTION

The present invention provides a novel surface engineering strategy that uses biomolecular interactions to immobilize surface modifying ligands on biomaterial architectures. The surface modified compositions resulting from the inventive method are useful in many contexts, including, but not limited to, scaffolds for tissue engineering and as vehicles for site specific drug delivery. In general, in a preferred embodiment, this biomolecular interaction is achieved by using an "anchor-adapter-tag" system, in which an adapter which can interact specifically and with high selectivity with an anchor molecule (present on the biodegradable surface) and a tag (bound to the ligand to be immobilized) simultaneously is used in attaching the ligand to the surface in a manner which is stable in vitro or in vivo. This has the advantage that the ligands may be presented in an active conformation, may be attached to the surface in an aqueous environment, and may be attached rapidly to the surface. In a particularly preferred embodiment, a polymeric material is utilized as the biomaterial architecture, and the anchor and tag comprise biotin, and the adapter comprises avidin or streptavidin.

The method of generating these novel surface modified biomaterials using an "anchor-adapter-tag" system involves (1) providing a biomaterial architecture, having an anchor attached thereto or incorporated therein; (2) contacting said biomaterial-anchor moiety with an adapter moiety; and (3) contacting said biomaterial-anchor-adapter moiety with a desired ligand having a tag incorporated therein to produce a biomaterial-anchor-adapter-tag-ligand moiety. In certain preferred embodiments, these novel compositions can be utilized in tissue engineering applications and also for applications in site specific drug delivery.

It will be appreciated that a two-component "anchor-tag" system can also be utilized in the present invention instead of the three-component "anchor-adapter-tag" system. Thus, in one preferred embodiment, the same moiety can be utilized for the anchor and the adapter, thus providing an "anchor-tag" system. In another preferred embodiment, the same moiety can be utilized for the adapter and tag, thus providing an alternate "anchor-tag" system.

The method of generating these novel surface modified biomaterials using an "anchor-tag" system involves (1) providing a biomaterial architecture, having an anchor attached thereto or incorporated therein; and (2) contacting said biomaterial-anchor moiety with a desired ligand having a tag incorporated therein to product a biomaterial-anchor-tag-ligand moiety.

In another aspect, the present invention provides a method for synthesizing a block co-polymer material having an anchor associated therewith. This method involves (1) providing a biodegradable polymeric material, wherein said polymeric material is capable of having an anchor moiety associated therewith and wherein said polymeric material has at least one functionality capable of further polymerization; (2) contacting said solution with an anchor moiety capable of associating with said polymeric material; and (3) subjecting said polymeric material having an anchor associated therewith to conditions capable of effecting further polymerization at a desired functionality to yield a desired anchor adapted block co-polymer material. This material can then be subsequently adapted into a variety of biomaterial architectures for use in the present invention as described above.

In another aspect, the present invention provides methods for site specific delivery of therapeutic agents comprising (1) providing a composition comprising a biomaterial architecture, wherein said architecture has a biological ligand attached thereto by a biomolecular interaction, and a therapeutic agent associated with the biomaterial architecture; and (2) contacting said composition with cells, wherein the ligand attached to the biomaterial architecture interacts with the cells to effect site specific delivery of the therapeutic agent to the cells.

In yet another aspect, the present invention provides methods for tissue engineering comprising (1) providing a scaffold having a biological ligand attached thereto, wherein said ligand is attached by a biomolecular interaction; (2) contacting said scaffold with cells, wherein said cells interact specifically with the ligand attached to the scaffold; (3) promoting cell growth and/or differentiation to generate tissue; and (4) implanting the tissue.

DEFINITIONS

"High affinity": As used herein, the term "high affinity" refers to an interaction with a $K_d$ of between $10^{-13}$ and $10^{-6}$ M.

"Interacts specifically": As used herein, the term "interacts specifically" means that the component interacts with at least 100-fold higher affinity (and preferably at least 500-fold, or at least 1000-fold, or at least 2000-fold higher affinity) with the intended binding component than with other molecules that may be encountered by either of the said components when administered to a patient.

DESCRIPTION OF CERTAIN PREFERRED EMBODIMENT

The present invention provides a novel surface engineering strategy that uses biomolecular interactions to immobilize surface modifying ligands on biomaterial architectures. The surface modified compositions resulting from the inventive method are useful in many contexts, including, but not limited to, scaffolds for tissue engineering and as vehicles for site specific drug delivery. In general, in one preferred embodiment, this biomolecular interaction is achieved by using an "anchor-adapter-tag" system, in which an adapter which can interact specifically and with high selectivity with an anchor molecule (present on the biodegradable surface) and a tag (bound to the ligand to be immobilized) simultaneously is used in attaching the ligand to the surface in a manner which is stable in vitro or in vivo. This has the advantage that the ligands may be presented in an active conformation, may be attached to the surface in an aqueous environment, and may be attached rapidly to the surface.

Figure 1:
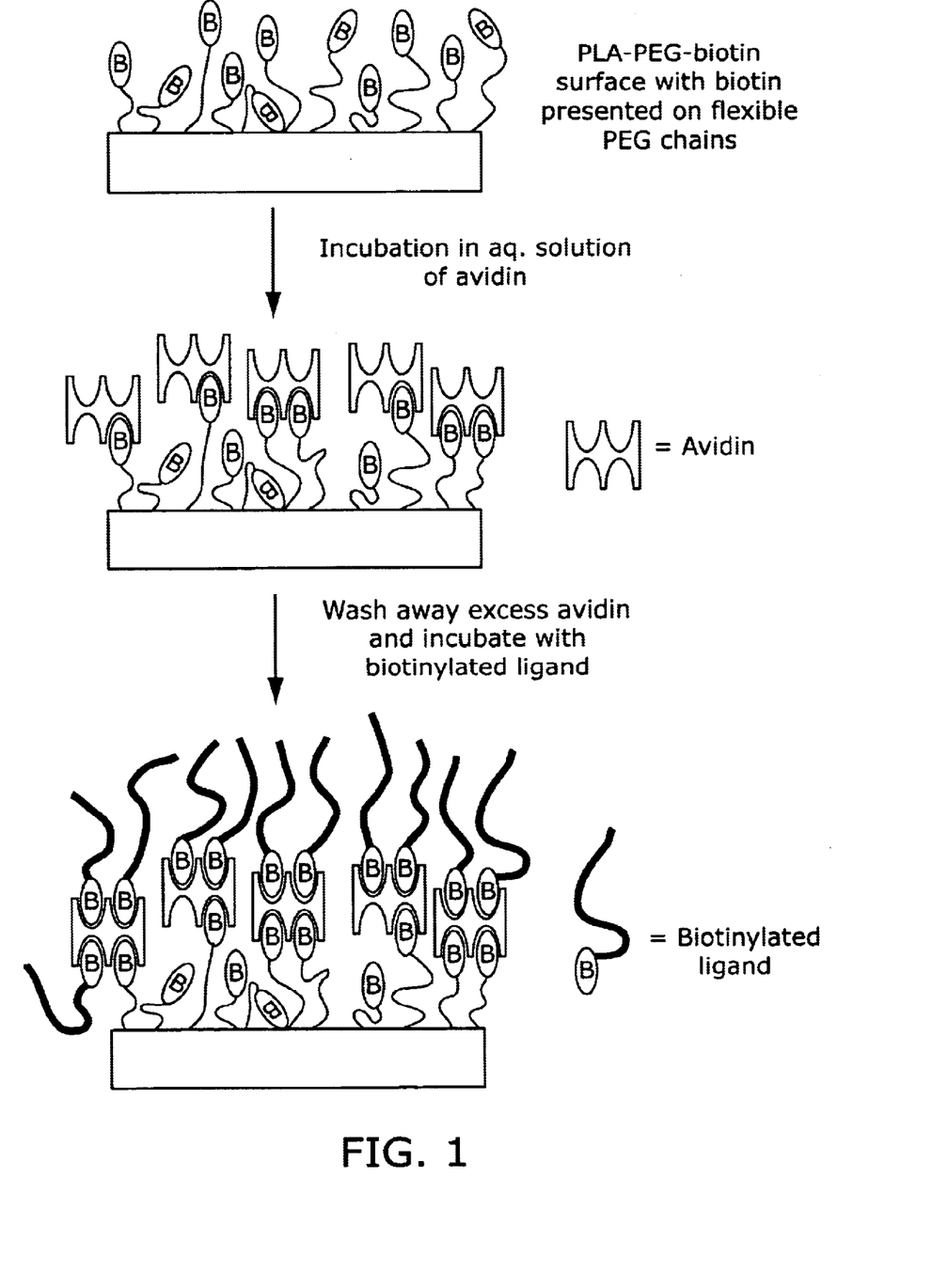
FIG. 1 depicts a particularly preferred embodiment of the present invention.

The method of generating these novel surface modified biomaterials involves (1) art providing a biomaterial architecture, having an anchor attached thereto or incorporated therein; (2) contacting said biomaterial-anchor moiety with an adapter moiety; and (3) contacting said biomaterial-anchor-adapter moiety with a desired ligand having a tag incorporated therein to produce a biomaterial-anchor-adapter-tag-ligand moiety. In certain preferred embodiments, these novel compositions can be utilized in tissue engineering applications and also for applications in site specific drug delivery. FIG. 1 depicts a particularly preferred embodiment of the present invention.

It will also be appreciated that a two-component "anchor-tag" system can also be utilized in the present invention instead of the three-component "anchor-adapter-tag" system. Thus, in one preferred embodiment, the same moiety can be utilized for the anchor and the adapter, thus providing an "anchor-tag" system. In another preferred embodiment, the same moiety can be utilized for the adapter and tag, thus providing an alternate "anchor-tag" system.

The method of generating these novel surface modified biomaterials using an "anchor-tag" system involves (1) providing a biomaterial architecture, having an anchor attached thereto or incorporated therein; and (2) contacting said biomaterial-anchor moiety with a desired ligand having a tag incorporated therein to product a biomaterial-anchor-tag-ligand moiety.

In another aspect, the present invention provides a method for synthesizing a block co-polymer material having an anchor associated therewith. This method involves (1) providing a biodegradable polymeric material, wherein said polymeric material is capable of having an anchor moiety associated therewith and wherein said polymeric material has at least one functionality capable of further polymerization; (2) contacting said solution with an anchor moiety capable of associating with said polymeric material; and (3) subjecting said polymeric material having an anchor associated therewith to conditions capable of effecting further polymerization at a desired functionality to yield a desired anchor adapted block co-polymer material. This material can then be subsequently adapted into a variety of biomaterial architectures for use in the present invention as described above.

Certain examples of preferred embodiments of preferred surface modified compositions, methods for making these compositions, and methods for using these compositions are described below, however these examples are not intended to limit the scope of the present invention.

Surface Modified Compositions:

As discussed previously, according to the method of the present invention, a biomaterial architecture is provided upon which to attach the desired ligand through either the "anchor-adaptor-tag" unit, or an "anchor-tag" unit. To achieve either of these biomolecular interactions, an anchor moiety must first be incorporated into the biomaterial architecture. The biomaterial architecture can be fabricated from any biodegradable and bioresorbable material that is capable of having an anchor moiety incorporated therein. It will be appreciated by one of ordinary skill in the art that the selection of the particular polymer material to be used will depend upon (1) the specific application for the surface modified composition and (2) the desired biomolecular interaction ("anchor-adaptor-tag" or "anchor-tag") to be utilized. In particularly preferred embodiments, the biomaterial architecture is a polymer. Suitable polymers include, but are not limited to polymers of poly(hydroxy acids), polyanhydrides, polyorthoesters, polyphosphazenes, polyphosphates, polycaprolactone, polyhydroxybutyrates, polyesters, polyamides, polysaccharides, polyproteins, and any copolymers or blends thereof. Once the polymer is selected, this polymer material can be contacted with a desired anchor material to form a polymer-anchor material. This material can be further modified, most preferably polymerized, to a block co-polymer material that can be subsequently modified to provide a biomaterial architecture. A particularly preferred block co-polymer material prepared for use in the present invention includes poly(lactic acid)-co-poly(ethylene glycol)-biotin (PLA-PEG)-biotin, as described in more detail herein.

As mentioned above, the selection of the particular polymer to be used will depend upon the desired biomolecular interaction utilized. For the "anchor-adapter-tag" embodiment, because the biomolecular interaction involves an interaction between the anchor, the adaptor and the tag, through the adapter, one of ordinary skill in the art will realize that the particular adaptor used must be able to interact with both the anchor and the tag. Thus, any multivalent adapter molecule with the necessary binding affinity for each of the components may be used. In but one example, the anchor and tag comprise biotin and the adapter is avidin or streptavidin. The valency of biotin is one, and that of streptavidin is 4. The $K_d$ for the binding of biotin to streptavidin/avidin is approximately $10^{-15}$ M. This binding is far stronger than many non-covalent interactions, and thus provides a system having an extremely high affinity and long lasting binding. In yet another example, a hapten may be used as the anchor and the same or a different hapten used as the tag, with an antibody of the requisite specificity/specificities used as the adapter. An antibody or antibody fragment may also be used as an anchor or a tag molecule. In this case the adapter molecule comprises epitopes for the anchor and/or tag, as appropriate.

In another preferred embodiment, a two-component "anchor-tag" system may be utilized. Thus, the anchor unit is able to be attached to the polymer and simultaneously mediate a biomolecular interaction with the tag unit bound to the desired ligand to be attached to the surface. Examples of bifunctional units include, but are not limited to, avidin, antibodies, streptavidin, biotin, and haptens. One of ordinary skill in the art will realize that any biological moiety may be utilized that is capable of attachment to the polymer and simultaneously mediating an interaction between the polymer and the ligand.

In but one example, incorporation of biotin into the desired polymer for use in the present invention may be achieved by attaching the biotin to the end group of the PEG (polyethylene glycol) block of the PLA-PEG polymer. Example 1 describes a typical synthesis for the production of the biotin containing PLA-PEG diblock polymer as shown below in structure 1.

STRUCTURE 1

In another example, an anchor molecule such as a protein, such as the antibody or antibody fragment discussed above, may be covalently bound to a block copolymer containing a polyalkylene glycol by reaction with the terminal hydroxyl group of the polyalkylene glycol. For example, the hydroxyl group can be reacted with a terminal carboxyl group or terminal amino group on the molecule to form an ester or amide linkage. Alternatively, the molecule can be linked to the polyalkylene glycol through a difunctional spacing group such as diamine or dicarboxylic acid. As will be appreciated by one of ordinary skill in the art, the reaction should be done under conditions that will not adversely affect the biological activity of the molecule being covalently attached to the polymer.

Once the anchor moiety is attached to the desired biomaterial architecture to form a biomaterial-anchor complex, or alternatively is contacted with an adapter moiety, thus producing a biomaterial-anchor-adapter complex, the biomolecular interaction can be completed by contacting either of these complexes with a ligand-tag moiety. As discussed previously, the tag moiety is a moiety selected for the ability to be incorporated/attached to the ligand and for its ability to bind either to the adapter moiety or the anchor moiety.

In particularly preferred embodiments, the ligand to be attached to the surface of the biomaterial architecture comprises a biologically active molecule. By biologically active molecule is meant any molecule that may have an effect on a biological process. It is preferred that the effect is to influence the growth or differentiation of cells. It will be appreciated that the biologically active molecule may inhibit or promote growth and/or differentiation of a particular type of cell. In certain preferred embodiments, the biologically active molecule is a peptide, protein, carbohydrate, nucleic acid, lipid, polysaccharide, or combinations thereof, for example a proteoglycan, or synthetic inorganic or organic molecule.

It is also preferred that the biologically active molecule is able to exhibit its activity while bound to the biomaterial architecture. However, it will be appreciated that the molecule may also be one that may be slowly released from the biodegradable surface and exhibits its activity when so released. It is particularly preferred that the biologically active molecule is a ligand for a cell surface receptor. It is particularly preferred that the molecule is a ligand for a receptor belonging to the integrin family of receptors, reviewed for example in Hynes "Integrins: versatility, modulation, and signaling in cell adhesion" Cell, 1992, 69, 11–25. Examples are receptors for fibronectin or vitronectin.

Specific examples of ligands that are capable of undergoing integrin-mediated molecular interactions that may be used include, but are not limited to adhesion proteins, for example fibronectin and vitronectin, or fragments thereof. Yet another example is the peptide sequence YIGSR, (SEQ ID NO:1), found in laminin (B1 chain) which binds to the 67 kDa laminin receptor found on many cell types. The peptide sequence IKVAV (SEQ ID NO: 2) is found in the A chain of laminin and binds the 110 kDa receptor and may induce neurite growth.

Additionally, many different peptides that contain the IKVAV (SEQ ID NO: 2) sequence may stimulate neurite extension. Any peptide that comprises a sequence of amino acids that is able to bind to a cell adhesion receptor may be used. The suitability of a peptide may be assessed by a means of measuring protein-protein interactions, as known to those skilled in the art. Suitability may also be assessed by functional assays, for example assessing the growth of a cell type of interest on a surface patterned with the peptide under consideration.

Still further examples include epidermal growth factor (EGF), nerve growth factor, insulin-like growth factor (IGF), basic fibroblast growth factor (βFGF), platelet derived growth factor (PDGF), transforming growth factor-β and related growth factors, for example bone morphogenetic proteins (BMPs), cytokines including interferons, interleukins, monocyte chemotactic protein-1 (MCP-1). It will be appreciated that these growth factors may also usefully be implanted/incorporated in the biocompatible, biodegradable material and released as the material degrades.

Further examples include dopamine, amine-rich oligopeptides, such as heparin binding domains found in adhesion proteins such as fibronectin and laminin, other amines and single basic amino acids, or monosaccharide binding to the asialoglycoprotein receptor on hepatocytes. For example, one can immobilize N-acetylglucosamine or lactose or polymerizable N-acetyllactosamine monomer, which can be polymerized to form an adhesive substrate.

Additionally, bone morphogenetic proteins (BMPs) may be useful for closure of defects in bone and basic fibroblast growth factor βFGF useful in inducing a vascularisation response. Slow release formulation, wherein the biologically active molecules are slowly released from the degrading polymer may be effective for these molecules.

Use of the Inventive Compositions

As will be appreciated by one of ordinary skill in the art, the compositions provided by the method of the present invention are useful in important biomedical application including, but not limited to, tissue engineering and site specific drug delivery, such as targeted nanospheres for gene delivery applications.

Towards that end, the present invention, in one aspect, provides a method for tissue engineering which involves (1) providing a biomolecular architecture having a biological ligand attached thereto through either of the biomolecular interactions described in detail above; (2) contacting said scaffold with cells, wherein said cells interact specifically with the ligand attached to the scaffold; (3) promoting cell growth and/or differentiation to generate tissue; and (4) implanting said tissue.

According to the method of the present invention, once the cells have grown and/or differentiated to a desired stage, depending on the particular clinical application, the tissue may be implanted. It is particularly preferred that the cells are seeded onto a biomaterial architecture in a bioreactor to promote growth (see, Langer and Vacanti, *Science*, 1993, 260, 920). As will be appreciated by one of ordinary skill in the art, the biodegradable material may be removed by hydrolysis and dissolution prior to implantation in the patient. Alternatively, the biodegradable material may still be present when the tissue is implanted, to provide support to the bioengineered tissue (for example, nerve) for a substantially predetermined period after surgical implantation, and degradation and/or metabolism may remove the material (or any remaining material after in vitro degradation/metabolism) in vivo. Important applications in which the inventive system may be utilized in tissue engineering include, but are not limited to, directed nerve regeneration and new blood vessel formation (vasculogenesis), and skin grafts.

In yet another aspect, the present invention provides methods for the site specific delivery of therapeutic agents to cells. This method involves (1) providing a composition comprising a biomaterial architecture, wherein said architecture has a biological ligand attached thereto by a biomolecular interaction, and a therapeutic agent associated with the biomaterial architecture; and (2) contacting said composition with cells, wherein the ligand attached to the biomaterial architecture interacts with the cells to effect site specific delivery of the therapeutic agent to the cells.

Therapeutic agents for use in the present invention include any pharmacologically active substances that produce a local or systemic effect in animals, preferably mammals, or humans. The term thus means any substance intended for use in the diagnosis, cure, mitigation, treatment or prevention of disease or in the enhancement of desirable physical or mental development and conditions in an animal or human.

Classes of therapeutic agents that can be used in the practice of the present invention include, but are not limited to, anti-AIDS substances, anti-cancer substances, antibiotics, immunosuppressants (e.g., cyclosporine), antiviral substances, enzyme inhibitors, neurotoxins, opioids, hypnotics, antihistamines, lubricants, tranquilizers, anticonvulsants, muscle relaxants and anti-Parkinson substances, anti-spasmodics and muscle contractants, miotics and anti-cholinergics, anti-glaucoma compounds, antiparasite and/or anti-protozoal compounds, antihypertensives, analgesics, anti-pyretics and anti-inflammatory agents such as NSAIDs, local anesthetics, ophthalmics, prostaglandins, anti-depressants, anti-psychotic substances, anti-emetics, imaging agents, specific targeting agents, neurotransmitters, proteins, cell response modifiers, vaccines, ribozymes, anti-sense agents, cytokines, immunotoxins, radiosensitizers, anti-edema agents, RNA, and combinations thereof.

As one of ordinary skill in the art will realize, the particular therapeutic agent to be utilized must be able to associate with the particular biomaterial architecture utilized. A particularly preferred biomaterial architecture includes, but is not limited to, nanoparticles.

Discussion of a Specific Preferred Embodiment Utilized in the Present Invention

To demonstrate a specific preferred embodiment of the present invention, a biodegradable polymer that employs a biological-recognition event to allow facile surface engineering with any type ligand on any material architecture has been engineered and utilized. The biodegradable polymer is composed of a block copolymer of biotinylated poly(ethylene glycol) (PEG) with poly(lactic acid) (PLA), called PLA-PEG-biotin. The bulk properties of this polymer are governed by the PLA block. The inherent biocompatibility of PLA leads to important considerations in device safety (Shalaby, S. W., "Biomedical Polymers: Designed-to-Degrade Systems", 1994, Hanser/Gardner, Cincinnati, Ohio; Atala et al., "Synthetic Biodegradable Polymer Scaffolds: Tissue Engineering" Birkhauser, Boston, 1997), and PLA degradation allows for formation of resorbable materials. Surface properties are determined by the PEG block which reduces nonspecific protein interactions (Andrade et al., *Adv. Chem. Ser.*, 1996, 248, 51), whilst the biotin moiety provides a universal linkage for surface engineering (Wong et al., *Science*, 1997 275, 820). As discussed previously, surface engineering is achieved using avidin as a bridge between the biotinylated polymer surface and biotinylated short ligand molecules. Since the tetrameric structure of avidin contains four biotin binding sites, avidin molecules immobilized on the material surface retain the ability to bind biotin. Therefore, as also discussed previously more generally, biotinylated molecules can be immobilized on the material surface at the site of the avidin immobilization.

Figure 2:
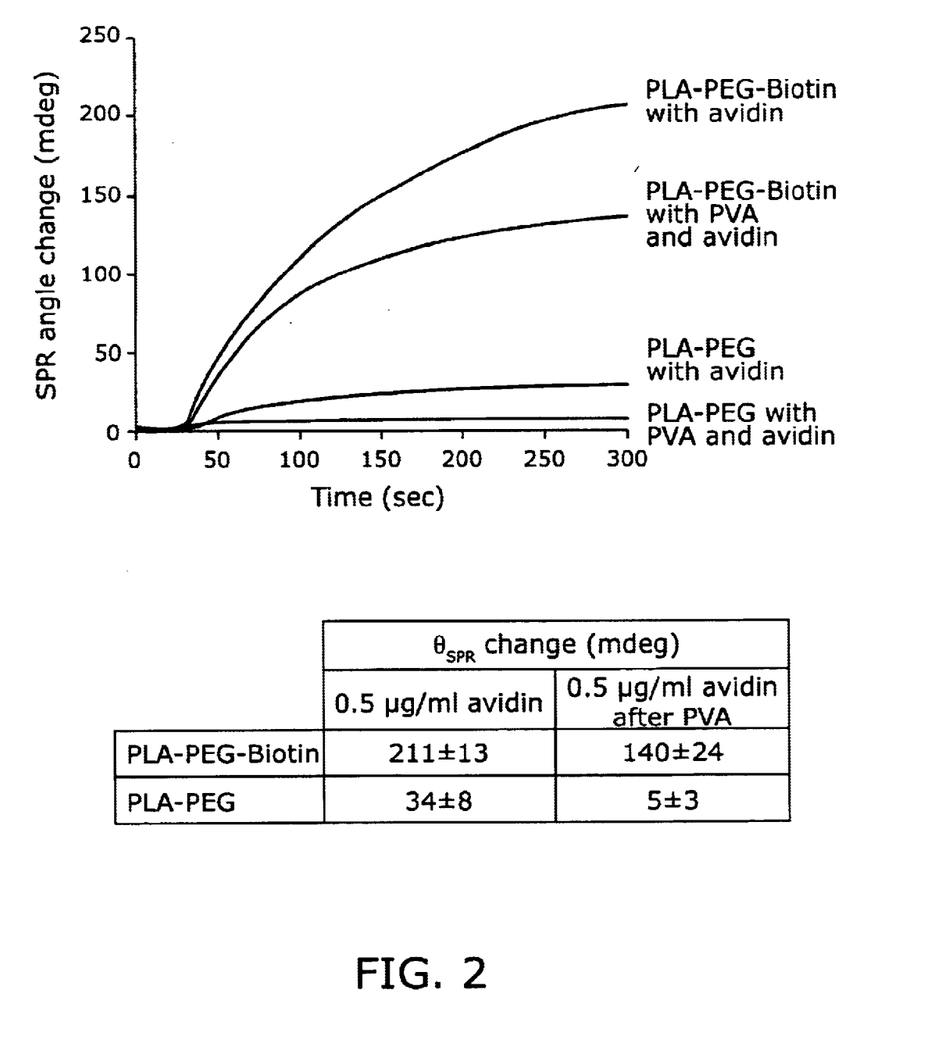
FIG. 2 depicts a comparison of avidin immunobilization on surfaces of PLA-PEG-biotin and PLA-PEG by surface plasmon resonance analysis.

The ability of the polymer to bind avidin was first measured under conditions encountered during the fabrication of polymeric materials. This was achieved using surface plasmon resonance analysis (SPR) to confirm and to measure the kinetics of avidin surface binding (FIG. 2). A large SPR angle (θ spr)) increase of 211±13 mdeg was recorded over a 300-s incubation period of the PLA-PEG-biotin with a 0.5 μm/mL avidin solution. In previous studies using SPR and atomic force microscopy (AFM), a θ spr increase of over 150 mdeg corresponded to at least a monolayer of protein coverage on polymer surfaces and self-assembled monolayers (Green et al., "Avidin and Streptavidin" in Methods in Enzymology: Avidin-Biotin Technology, Vol 184, Academic Press, New York, 1997). On control PLA-PEG surfaces, spr increased by only 34±8 mdeg under identical incubation conditions, indicating that only a small degree of nonspecific protein adsorption to the polymer surface has occurred. These data indicate a large amount of specific binding of avidin occurred to the PLA-PEG-biotin surfaces with very little nonspecific adsorption. The spr increase for PLA-PEG-biotin is very large, given that biotin is present only on the end of each PEG unit. The magnitude of the increase may be explained by the formation of a hydrated surface region that presents larger amounts of biotin than a two-dimensional biotinylated hydrophobic surface. Avidin binding to the PLA-PEG-biotin surface was found to plateau within 300 s after the introduction of the avidin solution. This suggests that the avidin incubation phase of surface engineering could be completed rapidly, ensuring that surface engineering is completed before material or ligand degradation occurs. A further control was performed to confirm that the large spr shift was generated by specific avidin-biotin binding. In this control, avidin was exposed to free biotin in an aqueous solution before exposure to the PLA-PEG-biotin film, hence, biotin binding sites on the avidin molecules were blocked and any avidin immobilization must be caused by nonspecific interactions. A spr increase of only 24±8 was recorded confirming the specific nature of the polymer to avidin interaction.

Additionally, in fabrication processes, newly formed surfaces must be stabilized by decreasing surface energy. This decrease is achieved by the adsorption of surfactants, such as poly(vinylalcohol) (PVA), to the material surface (Shakesheff et al., *J. Colloid Interface Sci.,* 1997, 185, 538). As a consequence of this adsorption, the surface chemistry of the material can be dominated by the surfactant and any beneficial surface property of a novel polymer can be masked. Therefore, it is important to establish that the PLA-PEG-biotin polymer maintains its avidin binding capability after surfactant stabilization. Using SPR analysis, it was found that exposure of a 1-mg/mL PVA solution to PLA-PEG-biotin surfaces prior to surface engineering caused a decrease in the amount of avidin surface immobilization. However, avidin binding to the surface was still significant. PVA adsorption to PLA-PEG-biotin surfaces caused θ spr to increase by 157±13 mdeg. Exposure of a 0.5 μg/mL avidin solution to this PVA-stabilized surface caused spr to increase by a further 140±24 mdeg (FIG. 2). Again, the magnitude of this increase indicates that the surface region of the PLA-PEG-biotin can bind large quantities of avidin. In control experiments, nonspecific adsorption of avidin to PVA-stabilized PLA-PEG surfaces caused spr to increase by only 5±3 mdeg (FIG. 2). It was concluded from this SPR study that surface engineering of materials fabricated from PLA-PEG-biotin can be performed after surfactant stabilization. Since functionalization is a postfabrication event, particle and film formation are not affected.

Figure 3A:
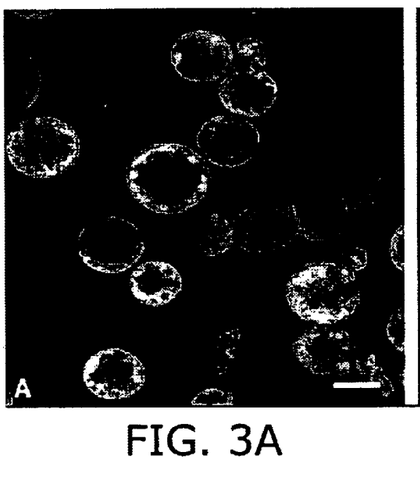
FIG. 3 depicts a fluorescence confocal micrograph of biodegradable microparticles.

We employed fluorescence confocal microscopy to prove that the biotin-avidin-biotin binding scheme can be used to surface engineer drug delivery microparticles composed of a PLA-PEG-biotin polymer. The micrograph of FIG. 3 (A) shows microparticles fabricated from PLA-PEG-biotin, with mean diameters of 5 μm, following incubation with avidin labeled with Texas Red (A-TxR). The image displays an even distribution of Texas Red across the microparticle surface indicating an even coverage of avidin. When microparticles fabricated from PLA-PEG underwent an identical incubation procedure, no fluorescence was detectable. This indicates that the A-TxR visible on the PLA-PEG-biotin microparticles was specifically bound to the biotinylated end groups.

Figure 4A:
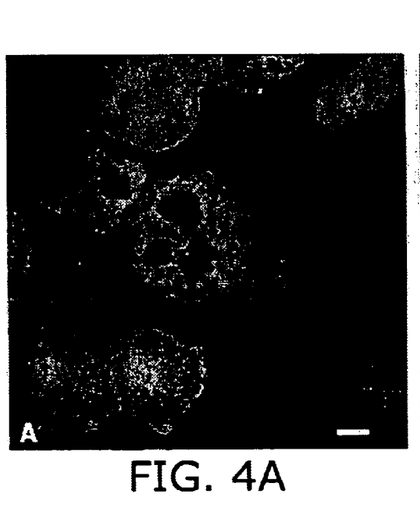
FIG. 4 depicts confocal micrographs of PLA-PEG-biotin microparticles following incubation with avidin-Texas Red and biotin-FITC.
Figure 4B:
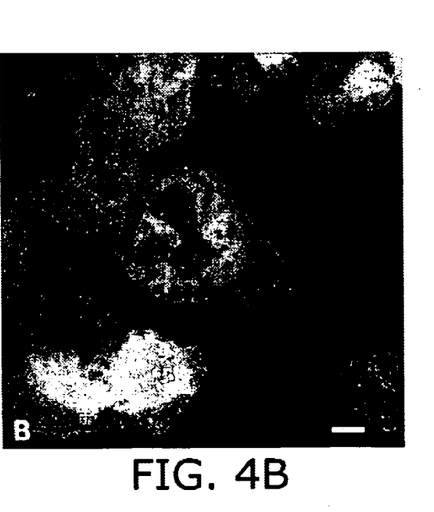

To prove that the surface immobilized avidin maintains the ability to bind biotinylated ligands, we performed a second incubation of the microparticles with biotin labeled with FITC (B-FITC). Fluorescence microscopy was then performed with simultaneous detection of FITC and Texas Red using separate optical channels for each label. For PLA-PEG-biotin microparticles, the distribution of B-FITC matched exactly the distribution of A-TxR. Complete surface coverage was recorded for both A-TxR and B-FITC on the majority of microparticles. However, a small number of microparticles had an incomplete coverage of A-TxR. These microparticles were ideal for comparing the surface area immobilization of A-TxR and B-FITC as shown by the micrographs in FIG. 4. In FIG. 4 (A and B) are shown simultaneously recorded distributions of A-TxR and B-FITC. There is a co-localization of the two molecules, with composite images showing the near 100% co-localization of the two probes.

We examined the immobilization of biotinylated ligand motifs, bridged by avidin to the material surface, maintained their ability to interact with cell surface receptors. We functionalized the surface of PLA-PEG-biotin films with a biotinylated polypeptide (biotin-(G)11-GRGDS) (SEQ ID NO: 3) that contains the cell adhesive tripeptide Arg-Gly-Asp (RGD). RGD is known to promote cell attachment and spreading through cell surface integrin receptors (Wilchek and Bayer, 1990). Immobilization of the biotin-(G)11-GRGDS (SEQ ID NO: 3) was confirmed by fluorescence binding studies in which avidin-immobilized PLA-PEG-biotin films were exposed to the biotinylated peptide, washed, and then exposed to a solution of B-FITC and rewashed. No fluorescence was detectable by confocal fluorescence microscopy indicating that biotin binding sites on the surface immobilized avidin were fully occupied with biotin-(G)11-GRGDS(SEQ ID NO: 3). In control experiments, exposure of the films to the B-FITC solution without prior exposure to the biotin-(G)11-GRGDS (SEQ ID NO: 3) generate films with high intensities of fluorescence.

Figure 5:
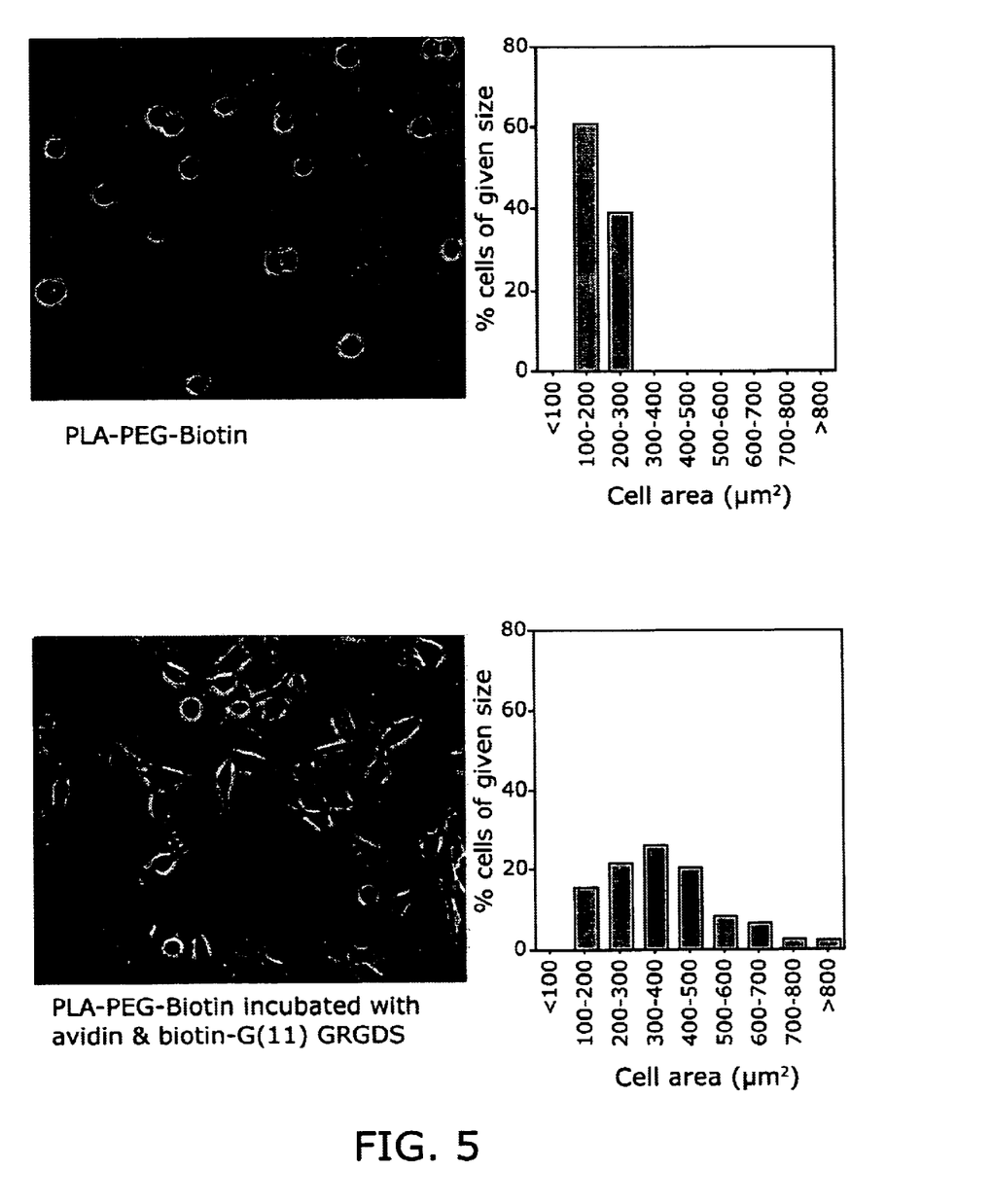
FIG. 5 depicts representative micrographs and cell area histograms of bovine aortic endothelial cells on the PLA-PEG-biotin surface and the RGD-functionalized surface 5 h after cell seeding.

Attachment and spreading of bovine aortic endothelial cells was observed on the PLA-PEG-biotin-avidin-biotin-(G)11-GRGDS (SEQ ID NO: 3) polymer surface at all time points, while no spreading was observed on negative controls which included samples composed of PLA-PEG, PLA-PEG-biotin, PLA-PEG-biotin-avidin, and PLA-PEG-biotin-avidin-biotin. In addition, no cell spreading was observed on samples of PLA-PEG-biotin which were incubated in biotin-(G)11-GRGDS (SEQ ID NO: 3), demonstrating the lack of nonspecific binding of the biotinylated RGD sequence to the polymer surface. The eleven glycine residue was provided to ensure clearance of the cell adhesive RGD sequence from the avidin binding pocket (Pierschbacher and Ruoslahti, *Proc. Natl. Acad. Sci.,* U.S.A.,1984, 81, 5985; Green, "Avidin and Streptavidin" in Methods in Enzymology: Avidin-Biotin Technology, Vol 184, Academic Press, Inc., New York, 1990; Beer et al., *Blood,* 1992, 79, 117). FIG. 5 shows images of cells on the PLA-PEG-biotin and PLA-PEG-biotin-avidin-biotin-(G)11-GRGDS (SEQ ID NO: 3) surfaces along with a histogram of measured cell area for each sample.

Experimental Details

EXAMPLE 1

Polymer Synthesis

A typical synthesis for the production of the biotin containing PLA-PEG block copolymer is as follows: First, α-amine γ-hydroxy PEG (Shearwater Polymers, Inc., average molecular weight, 3.8 K) was stirred with NHS-biotin (Fluka) and triethylamine in dichloromethane and acetonitrile at room temperature under argon overnight. The biotinylated PEG was then isolated by vacuum filtration and dried from toluene azeotrope. Secondly, (l-)lactide was polymerized from the γ-hydroxy PEG-biotin in refluxing toluene to give PLA-PEG-biotin. The final polymeric material was recovered by dissolution in dichloromethane and precipitation in cold ether. $^1$H NMR at each stage confirms the attachment of biotin to the PEG chain. Also, (l-)lactide monomer feed ratios corresponded to $^1$H NMR integrations for PLA signals versus PEG signal, indicating efficient conversion of the lactide monomer to PLA. Polymer molecular weights were determined from $^1$H NMR using the PEG signal as a reference. Gel permeation chromatography revealed one peak, indicative of pure material. Polymer molecular weight can be varied from lactide feed ratios. The PLA molecular weight for this study was 9.2 K. In a similar fashion, the control material, PLA-PEG, was prepared from the monofunctional α-methoxy γ-hydroxy PEG (Shearwater Polymers, Inc., average molecular weight, 3K).

EXAMPLE 2

SPR Analysis

The SPR instrument (Johnson & Johnson Clinical Diagnostics, Buckinghamshire, US) had a Kretschmann configuration (Kretschmann, 1971) and utilized a monochromatic laser light source with a wavelength of 780 nm. SPR sensor slides were produced by vapor deposition of a thin film of silver (approximately 50 nm thick) onto glass slides. Thin films of the polymer under analysis were formed on the SPR sensor surface by spin casting 100 uL aliquots of a 1-μg/mL polymer solution in chloroform at 2000 rpm. During the experiment, the instrument measured the angle of minimum reflectivity, termed the SPR angle (θ SPR), as detected by the photodiode array. This minimum was plotted against time. For experiments examining the binding of avidin to the polymer in the absence of PVA, phosphate buffer (100 mM, pH 7.4) was flowed over the polymer surfaces for 240 s at a flow rate of 0.249 mL/s to obtain a stable baseline value for θ SPR. Then 1 mL of the avidin solution (0.5 μg in 10 mM phosphate buffer, pH 7.4) was injected into the sample flow cell at 0.249 mL/s, using an electronically controlled Rheodyne Type 6 port valve. After 250 s of avidin injection, buffer was washed through the flow cell for 375 s at 0.240 mL/s. For experiments investigating the amount of avidin binding after exposure of the polymer surface to PVA, 1 mL of an aqueous PVA solution (88 mol % hydrolyzed, 10 mg/mL) was injected into the flow cell over a period of 350 s, followed by a 375-s buffer wash. Then the surface was exposed to avidin using an identical procedure to that described above. For all SPR results presented, θ SPR is quoted after 300 s of avidin solution injection. In all cases the value of SPR remained constant after 300 s during the replacement of avidin solution with buffer.

EXAMPLE 3

Fluorescence Binding Studies

Microparticle Fabrication:

Microparticles were produced using a single emulsion technique in which 10 mL of a 25 mg/mL solution of the polymer in dichloromethane was homogenized for 2 min in 250 mL of a 0.1% aqueous PVA solution (PVA 88% hydrolyzed, PolySciences Inc., Warrington, Pa.). The resulting emulsion was stirred for 4 h to allow the dichloromethane to evaporate. The microparticles were collected by centrifugation at 5,000 rpm for 10 min and washed three times in distilled water and then lyophilized. Particle size analysis was performed with Coulter Counter Particle Sizer. All batches of microparticles were found to exhibit mean diameters of between 3.6 and 7.2 um.

Fluorescent Labeling of Microparticles:

A 10-mg amount of microparticles, fabricated from PLA-PEG biotin or PLA-PEG, was resuspended in 750 μL of phosphate-buffered saline (PBS). Then, 750 μL of an aqueous 200-ug/mL avidin-Texas Red (A-TxR) solution was added to the suspension, and the suspension was incubated at 37° C. for 20 minutes. Microparticles were collected by centrifugation and washed three times in PBS. Next, the microparticles were incubated in biotin-FITC (B-FITC) using the same concentration as employed for avidin. Control experiments were performed in which nonlabeled avidin and biotin were substituted for the A-TxR and B-FITC. No fluorescence was recorded in the substituted samples. For studies requiring the simultaneous detection of FITC and Texas Red, control experiments were performed to ensure that the emission from one fluorescent label did not result in the false detection of the second label. Finally, the microparticles were suspended in PBS and sealed in microwell chambers for microscopic examination.

Figure 3B:
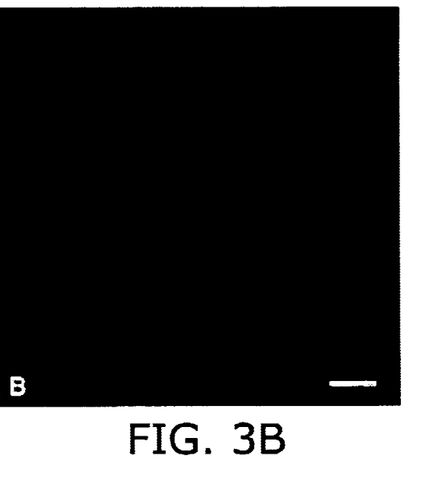

Fluorescence Microscopy:

Microparticles from the biotin-avidin-biotin fluorescent study (FIGS. 2 and 3) were viewed using a Sarastro 2000 confocal laser scanning microscope (CLSM) (Molecular Dynamics, Sunnyvale, Calif.) fitted with a 25-mW argon-ion laser. The microscope was configured for dual channel fluorescent imaging with simultaneous 488- and 514-nm excitation, 10% laser transmission, and 18-mW laser power. Emission spectra (>600 nm) from the A-TxR were collected by a photomultiplier tube (channel 1) operated at a voltage 500–600 V. Another optical path was selected for emission spectra emitted from the B-FITC and was simultaneously collected through a 540-nm filter with a 15-nm bandwidth. Fields of particles were randomly selected and images were recorded in a 512 or $10^{24}$ image size format using a 60×1.4 numeric aperture objective.

EXAMPLE 4

Cell Studies

Cell Culture

Bovine aortic endothelial cells were a generous gift from Dr. Keith Gooch. The cells were maintained in a low-glucose Dulbecco's Modified Eagles Medium (DMEM) supplemented with 10% fetal bovine serum, 0.5% penicillin, 0.5% streptomycin, and 1% L-glutamine in a humidified incubator at 37° C. and 5% $CO_2$. Cells were passaged by trypsinization before reaching confluence, usually every 5th day. Fresh media was added every other day.

Sample Preparation:

Films of PLA-PEG-biotin or PLA-PEG were prepared by drop casting 100 μL aliquots of the 10-mg/mL solution of the polymer in chloroform onto circular glass coverslips. Six sample types were prepared for the cell studies: PLA-PEG, PLA-PEG-biotin. PLA-PEG-biotin incubated with avidin, PLA-PEG-biotin incubated with avidin and biotin, PLA-PEG-biotin incubated with biotin (G)11-GRGDS (SEQ ID NO: 3), and PLA-PEG-biotin with avidin and biotin (G)11-GRGDS (SEQ ID NO: 3). The films on coverslips were placed in 6-well plates and sterilized under UV light for 10 minutes. The films were washed 3 times with sterile phosphate-buffered saline prior to seeding with cells.

Cell spreading Experiment:

Bovine aortic endothelial cells between passages 7 and 9 were removed from tissue culture flasks by trypsinization, pelleted by centrifugation, resuspended, washed 3 times, and diluted to the appropriate concentration in serum-free DMEM. Approximately 10,000 cells/cm$^2$ were added to each sample in serum-free medium, and the plates were returned to the incubator for the duration of the experiment.

A Nikon Diaphot TMD inverted microscope equipped with a ×20 phase contrast objective and a Hitachi HV-C20 high resolution CCD video camera was used to visualize spreading cells 1, 3, 5 and 24 h after cell seeding. Images were digitized using NIH Image (v 1.60) image analysis software running on a Power Macintosh 7100/66. Images from five regions of 0.5 mm$^2$ each from each sample were captured and saved for analysis. Cell area was measured by tracing the projected outline of the cell for at least 75 cells from each sample at each time point. Only cells that were not in contact with surrounding cells were analyzed.

What we claim is:

1. A composition comprising a biomaterial architecture having a ligand attached thereto through a biomolecular interaction, wherein said biomaterial architecture comprises a biodegradable polymer having an anchor moiety incorporated therein, and wherein said biomolecular interaction is effected by an anchor-adapter-tag unit comprising the anchor, a tag attached to the ligand, and an adapter that links the anchor and the tag, wherein the unit is retained on the polymer by the anchor, wherein the anchor and tag comprise the same or different hapten, and the adapter comprises an antibody having specificity for the hapten(s).

2. A composition comprising a biomaterial architecture having a ligand attached thereto through a biomolecular interaction, wherein said biomaterial architecture comprises a biodegradable polymer having an anchor moiety incorporated therein, and wherein said biomolecular interaction is effected by an anchor-adapter-tag unit comprising the anchor, a tag attached to the ligand, and an adapter that links the anchor and the tag, wherein the unit is retained on the polymer by the anchor, further comprising a therapeutic agent, wherein said therapeutic agent is formulated with the polymer to generate a biomaterial architecture having a therapeutic agent encapsulated therein.

3. The composition of claim 1 or 2, wherein said polymer is poly(lactic acid)-co-poly(ethylene glycol) (PLA-PEG).

4. The composition of claim 1 or 2, wherein said biodegradable polymer is selected from the group consisting of polymers of poly(hydroxy acids), polyanhydrides, polyorthoesters, polyphosphazenes, polyphosphates, polycaprolactone, polyhydroxybutyrates, polyesters, polyamides, polysaccharides, and polyproteins.

5. The composition of claim 1, further comprising a therapeutic agent, wherein said therapeutic agent is a ligand attached to the biomaterial architecture through a biomolecular interaction.

6. The composition of claim 1, 2, or 5, wherein said ligand is selected from the group consisting of peptide, protein, carbohydrate, nucleic acid, lipid, polysaccharide, inorganic molecule, organic molecule, and combinations thereof.

7. The composition of claim 1 or 2, wherein said biomaterial architecture comprises a particle.

8. The composition of claim 1 or 2, wherein said biomaterial architecture comprises a nanosphere or microsphere.

9. The composition of claim 1 or 2, wherein said biodegradable polymer is a copolymer of a polymer selected from the group consisting of poly(hydroxy acids), polyanhydrides, polyorthoesters, polyphosphazenes, polyphosphates, polycaprolactone, polyhydroxybutyrates, polyesters, polyamides, polysaccharides, and polyprotains.

10. The composition of claim 1 or 2, wherein said biodegrad polymer is a blend of any of the polymers selected from the group of polymers consisting of poly(hydroxy acids), polyanhydrides, polyorthoesters, polyphosphazenes, polyphosphates, polycaprolactone, polyhydroxybutyrates, polyesters, polyamides, polysaccharides, and polyproteins.

11. The composition of claim 1, wherein said therapeutic agent is a ligand attached to the biomaterial architecture through a biomolecular interaction.

* * * * *